United States Patent [19]

Schvoerer et al.

[11] Patent Number: 4,939,372

[45] Date of Patent: Jul. 3, 1990

[54] PROCESS FOR MARKING OBJECTS BY THE USE OF MEMORY MICRO-CRYSTALS AND MARKERS FOR ITS IMPLEMENTATION

[75] Inventors: Max Schvoerer; Claude Ney, both of Bordeaux, France

[73] Assignee: Microtrace International, Luxembourg, Luxembourg

[21] Appl. No.: 278,945

[22] PCT Filed: Feb. 12, 1988

[86] PCT No.: PCT/FR88/00078

§ 371 Date: Oct. 12, 1988

§ 102(e) Date: Oct. 12, 1988

[87] PCT Pub. No.: WO88/06330

PCT Pub. Date: Aug. 25, 1988

[30] Foreign Application Priority Data

Feb. 13, 1987 [FR] France .............................. 87 01970

[51] Int. Cl.$^5$ ............................................. G01N 23/00
[52] U.S. Cl. ................................. 250/484.1; 250/337
[58] Field of Search ................. 250/484.1 A, 484.1 B, 250/484.1 R, 337; 436/173

[56] References Cited

U.S. PATENT DOCUMENTS 3,657,085 4/1972 Hoffmeister et al. .

FOREIGN PATENT DOCUMENTS 1601856 9/1968 France .
2007339 3/1969 France .
2556867 12/1983 France .

OTHER PUBLICATIONS

"Effect of a Low-Frequency Magnetic Field on NMR and Dynamic Nuclear Polarization of Nuclei in Al$_2$O$_3$:Cr$^{3+}$ and CaF$_2$:Tm"; S. A. Kazanskii et al., Sov. Phys. JETP 57 (6), Jun. 1983, pp. 1345–1350.

Sazed et al, "Y and N Dosimetry Based on Elec. Conduct. of TL Photphors", Nucl. Instrum. & Meth., No. 2 (Feb. 1987).

Sutton et al, "TL Dating Using Zircon Grains from Archaeol. Ceramic", Archaemetry 18, 2(1976), pp. 125–134.

Primary Examiner—Janice A. Howell
Assistant Examiner—Richard Hanig
Attorney, Agent, or Firm—Robert J. Koch

[57] ABSTRACT

Method for marking objects by the use of memory micro-crystals, consisting in choosing one or several micro-crystals, of doping each micro-crystal, if this has not already occurred naturally, with any one of the rare earths and transitional metals, in irradiating the micro-crystal or micro-crystals with high-energy rays or particles, according to a predetermined dosage in order to trap the charge carriers, released by ionization of the atoms, while in their energetically metastable state, said process consisting also in applying a predetermined quantity of the micro-crystal or micro-crystals irradiated by said method, to at least one predetermined part of the object, and in safely recording, for the purpose of later comparison, the characteristics, implantation and conditions under which dopage and irradiation of the micro-crystal or micro-crystals took place. Application to the authentication of objects.

10 Claims, 1 Drawing Sheet

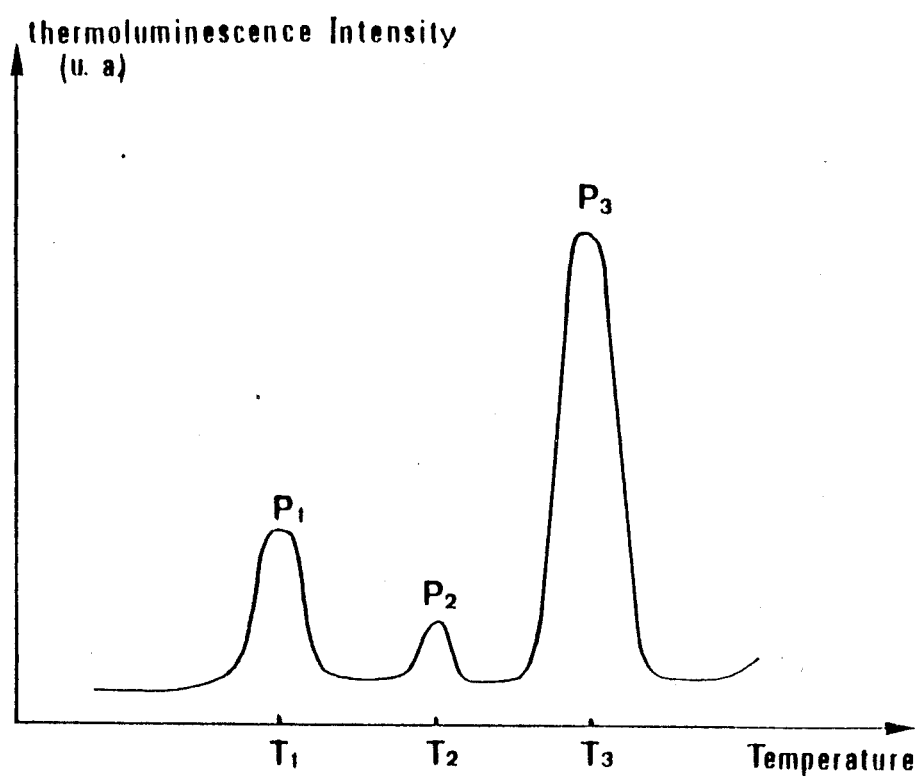

PROCESS FOR MARKING OBJECTS BY THE USE OF MEMORY MICRO-CRYSTALS AND MARKERS FOR ITS IMPLEMENTATION

FIELD OF THE INVENTION

The present invention relates to a process for marking any objects by means of memory micro-crystals for recognizing and subsequently authenticating said object in any circumstances by indentification of a specific signature contained in the micro-crystals and introduced during marking operations.

SUMMARY OF THE INVENTION

The aim of the invention is to provide a reliable means for marking an object capable of keeping a signature or information specific to the object for a very long time despite natural risks and attempts of all kinds to suppress or alter the signature, for subsequently authenticating the object bearing the marker by reading said signature and comparing it with a reference signature which is the image of the signature introduced into the marker incorporated in the authentic object and kept in a safe place.

For this, the invention provides a process for marking objects by memory micro-crystals, characterized in that it consists in choosing, from crystals having a guarantee of stability of the crystal under the conditions of introduction and reading of a signature or information specific to the object, one or more micro-crystals in the form of a powder of very small sized crystals, in doping each micro-crystal, if it is not done naturally, by any one of the rare earths and transition metals, at the rate of about 100 to 1000 ppm by weight with respect to the micro-crystal, in emptying the trap centres present in the micro-crystal or micro-crystals by heating, in irradiating the micro-crystal or micro-crystals with high energy rays or particles, according to a predetermined dosage so as to trap the charge carriers released by ionization of the atoms, in a number proportional to the dose, while in their energetically metastable state, the choice of the micro-crystal or micro-crystals and the doping and irradiation conditions determining said signature or information specific to the object, in applying in at least one given position of the object a given amount of the micro-crystal or micro-crystals thus irradiated and in keeping in a safe place, for subsequent comparisons, the characteristics, the implantation and doping and irradiation conditions of the micro-crystal or micro-crystals.

Thus, if authentication of such a marked object is one day required, it will be sufficient to collect a part of the micro-crystal or micro-crystals applied to the object, read the contents of the signature carried by the marker formed by said micro-crystal or micro-crystals and to compare this data with that kept at the time of marking the authentic object. Such work of authentication will of course be carried out by a competent and approved laboratory which will therefore have access to said data kept in a safe place and will know how to go about recovering the micro-crystals.

Reading consists in locating said charge carriers trapped in the specific defects of the micro-crystal or micro-crystals by using in a way known per se the physical phenomena induced by radiation, for example the modification of optical absorption, of photoconductivity, of the paramagnetic electronic resonance, of the photoluminescence or the thermoluminescence.

The marker of the present invention, which is the material carrier of the signature or information specific to to object to be marked, is a crystal or a glass splinter of very small dimensions, generally less than 50 micrometers. It may be synthetic or natural. In all cases it contains, by voluntary doping (synthetic carrier) or spontaneous doping (natural carrier) the structural defects which make it able to receive and store said signature. As carriers there may be mentioned, among others, fluorines of type $CaF_2$, Lif, sulphates of type Ca, Ba, $SrSO_4$, aluminas or aluminates of the type $Al_2O_3$, certain silicates, borates, carbonates, the quartzes, the feldspaths.

The above carriers are quite particularly suitable but, generally, all clear coloured or transparent crystals are likely to present the required characteristics, namely a good structural stability in time and under the conditions of introducing the signature (irradiation) and restoring it (reading) and a good storage capacity as well as a good resistance to ordinary chemical agents.

Certain crystals, such as certain fluorides, are naturally doped in the desired proportions, at about 100 to 1000 ppm of rare earth and have suitable defects.

For synthetic crystals, the oxidation-reduction conditions for the preparation of doping are advantageously modulated so as to obtain the desired number of defects conjointly with the introduction of the optimum amount of dopant.

In the present invention, by crystal is meant a general state of solids structurally very well organized, this term covering here not only crystals in the scientific sense but also less well organized solids up to the amorphous state (glasses).

By way of example, in order to obtain a suitable micro-crystal, calcium sulphate in the gypsum state is placed in sulphuric acid with dysprosium oxide at the rate of about 100 ppm by weight. It is boiled and in the bottom of the container $CaSO_4$ Dy cystals are obtained in which some dysprosium atoms replace certain calcium atoms.

One of the rare earths and any one of the transition metals may be suitable, the proportion of rare earth or of transition metal varying with their nature.

The optimum rare earth content of the doped crystal corresponds for example to the maximum amplitude of the intensity of the electronic paramagnetic resonance when the crystal is subjected to such radiation or to the maximum intensity of the thermoluminescence if this other method of measurement is used.

The modifications of said oxidation-reduction conditions consist practically in modifying only the oxygen content. This variation of the oxygen content results in a variation of the number and depth of the defects which are also called trap centres.

It was mentioned above that the insertion of the signature in the doped micro-crystal consisted in irradiating the latter with high energy rays or particles.

They may for example be X, gamma, UV rays or alpha, beta particles, ions, etc...

Such irradiation ionizes the atoms and traps the released charge carriers in specific defects (or trap centres) of the crystal where they accumulate in energetically metastable conditions. Depending on the energy depth of the trap centres, the duration of retention of these carriers may be very long; in some crystals it reaches tens of thousands of years. The defects or trap centres are generally gaps or aggregates of atomic gaps or chemical impurities. Their nature and their situation in a crystal or a glass are specific to the solid considered and its method of preparation. The advantage of the action on the method of preparing the doped crystal (modifications of the oxidation-reduction conditions) resides in the possibility thus offered of increasing the number of trap centres and so of introducing a more diversified signature as will be seen further on.

The irradiation dose, expressed in rads, may vary. It determines proportionally the number of electrons snatched form the anions and which become free. These electrons are then captured on the external layer of the rare earths which pass from the stable state 3+ to the state 2+ which is metastable but which may last a very long time.

The irradiation dose therefore determines proportionally the number of rare earth atoms in state 2+.

It should be noted that prior to incorporation of the signature in the crystal, it is preferable to empty the trap centres so as to reset as it were the memory of the crystal to zero. That is achieved by simply heating the crystal to a sufficient temperature, about 450° C.

Irradiation incorporates then, in the doped crystal, information which is energetically well attached for it will require a considerable amount of energy to cause the rare earth atoms to swing from state 2+ to state 3+. These energy amounts will of course have to be applied to the crystals during reading of the incorporated signature. If it is a question for example of reading by thermoluminescence, it will be necessary to heat the crystals to about 450° C. If it is a question of electronic paramagnetic resonance reading the crystals will need to be plunged in a very intense magnetic field of the other of 50 000 gauss. Other reading techniques are of course possible, as mentioned above.

These energies cannot as a rule be used without having located the micro-crystals on the object, isolated them, characterized them and subjected them to a powerful laboratory treatment, so many cumulative steps which are the guarantee of the perenniality of the integrity of the marker. At the time of reading, for example by thermoluminescence, as the temperature increases the heat will successively empty the trap centres of the doped crystal beginning with the energentically shallower traps. Each electron driven from a trap will go towards the rare earth whose energization is followed immediately by radiative de-energization (photon captured and measure by the measuring apparatus used in thermoluminescence).

BRIEF DESCRIPTION OF THE DRAWING

In the single figure accompany the present description, an example has been shown of a curve for reading a signature carried by a marker of the invention by thermoluminescence.

DETAILED DESCRIPTION OF THE PREFERRED EMBODIMENT

The temperature is plotted as abscissa and the ordinates shown the intensity of the thermoluminescence in arbitrary units (UA).

The marker in question is for example a calcium fluoride crystal doped with cerium $Ce^{3+}$.

In the figure three successive peaks can be seen P1, P2, P3 of unequal heights and corresponding to three different temperatures T1, T2, T3.

The position of the peaks along the axis of the abscissa is characteristic of the type of crystal.

The relative height of the peaks is characteristic of the crystallogenesis conditions.

The intensity of the high temperature peak (peak P3 of highest intensity) is directly proportional to the irradiation dose at the time of incorporating the signature in the doped crystal.

Finally, the colour of the thermoluminescent emission, which is possibly analysed, is characteristic of the rare earth doping the crystal.

Thus, the thermoluminescence reading curve, such as the one shown in the figure, forms a sort of identity photograph characteristic of the marker. By the choice of the type of crystal, the type of dopant, the crystallogenesis conditions (modification of the oxidation-reduction conditions) and of the irradiation method and dose of the doped crystal, several characteristic data are associated which make possible a very large number of different combinations, each forming a unique signature which will be incorporated in the object to be marked by the marker, i.e. the irradiated doped crystal carrying said signature or information specific to the object concerned, by appropriate means in one or more chosen positions on the object.

Incidentally, it should be noted that several doped and irraidated micro-crystals having different signature can be combined to form a marker.

By object is meant any material support made from any material, flat (documents of all sorts), or bulky.

Examples of objects which can be marked using the present invention include: art work, books, jewelry, furs, stamps, or any other objects whose identity it is desirable to be able to authenticate.

In one method of applying a marker of the invention to an object, the micro-crystals or the association of micro-crystals is mixed with a quick setting glue. Several commercially available glues have been tested and may be suitable because of their transparency and their non fluorescence under UV radiation and because they possess a specific solvent. The glue must also be adapted to the nature of the object to be marked.

The method of applying the glue comprising the micro-crystals depends on the nature of the object. A brush or a syringe may be used, or it may be applied electrically, by transfer, ect. . . One or more applications may be made to the same object, with the same sample of glue or a combination of samples.

Application of the marker must be as discreet as possible and must neither harm nor destroy the marked object.

Apart from the difficulty of detecting on the object the position or positions where the glue is applied, which is transparent and only comprises a very small amount of micro-crystals, such a marker is insenitive to current temperature rises (incandescent lamp, thermal radiator, very hot water, ect. . .), to an examination under UV light, an Xray using X or neutron rays, as well as an intense magnetic field.

There is therefore no danger of the marker losing its specific information either by an intentional action or followingl circumstances.

It should be noted in this connection that though an X ray or an ultra-violet light observation is likely to modify a part of the message, namely a shift towards the top of peak P3, which corresponds to an increase of the irradiation dose, such a modification does not denature the overall signature of the marker, which remains pertinent, the modification of one of the pieces of information being in no wise a latent defect. Similarly, in the case of fire, the shallower traps in the doped crystal will be emptied but the other will continue to exist and the signature will not be lost.

The only practical risk which the marker runs is a destructive action which is voluntary or not, e.g. a mutilating action, a mechanical action, etc. . . In this case, it is of course impossible to authenticate the object.

In all the other cases, location and reading of a part of the micro-crystals applied to the object will make its authentication possible. Sufficient micro-crystals are course left in place for possible subsequent authentication.

The micro-crystals of the marker, once located, are recovered by scratching or dissolution of the glue which holds them on the marked object.

For subsequent authentication purposes, at the time of applying the marker (chosen form a batch which may be very large of different markers previously produced and stored) a technical docket is drawn up for the marked object. Such dockets will form a data bank available to a small number of skilled and approved laboratories whose high specialization and international scientific audience will be guarantees of quality and strictness with respect to the authentication which they alone will be able to practice.

Finally, the invention is obviously not limited to the embodiments described above but covers on the contrary all variants thereof particularly in so far as the nature of the crystal and of the rare earth which may be used are concerned, the methods of irradiation and reading of the doped crystals, as well as the nature of the vehicle carrying the marker or markers and which is applied to or incorporated in the surface or in the mass in one or more positions of the object to be marked and the technique for positioning on said vehicle.

We claim:

1. A method for marking objects using memory micro-crystals comprising the steps of:
    selecting micro-crystal powder of very small sized crystals exhibiting stability under conditions for introduction and reading of object specific information;
    doping each micro-crystal;
    emptying trap centers present in said micro-crystals;
    irradiating said micro-crystals with a predetermined dose of high energy rays or particles to trap charge carriers released by atom ionization;
    wherein an amount of said charge carriers is trapped proportional to said dose and a metastable state of said micro-crystals determines object specific identification or signature in accordance with said crystal selection and doping and irradiating conditions;
    applying an amount of said micro-crystals to an object in a fashion calculated to maintain said micro-crystals for subsequent comparisons.

2. A method according to claim 8, wherein said crystal is chosen from the group consisting of fluorides, sulphates, aluminas, aluminates silicates, borates, carbonates, quartzes, and feldspars.

3. A method according to claim 2 further comprising the step of adjusting oxygen content of said crystal to modify the number and depth of the trap centers capturing said released charge carriers during the doping step.

4. A method according to claim 1, wherein said subsequent comparisons are carried out by taking a part of the micro-crystal or micro-crystals from the object to be authenticated, to recover said signature or information specific to the object .

5. A method according to claim 4, further comprising the step of reading the doped micro-crystal or micro-crystals by a step chosen from the group consisting of measurement of optical absorption modification, measurement of photoconductivity, measurement of electronic paramagnetic resonance, measurement of photoluminescence, and measurement of thermoluminescence.

6. A method according to claim 1, further comprising the step of mixing said micro-crystals with a vehicle formed by a glue, which is transparent and not fluorescent, in ultra-violet light;
    and applying said glue to or in the object.

7. A method according to claim 1 wherein said step of doping is with rare earth elements at a rate of 100 to 1000 ppm by weight.

8. A method according to claim 1 wherein said step of doping is with transition metals at a rate of 100 to 1000 ppm by weight.

9. A method according to claim 1 wherein said step of emptying is performed by heating.

10. Marker for implementing an object authenticating process comprising one or more micro-crystals doped with a rare earth or a transition metal, in the form of a powder with crystal dimensions of the order of 50 micrometers or less, each irradiated with high energy rays or particles.

* * * * *